United States Patent [19]

Freemon

[11] 4,308,629
[45] Jan. 5, 1982

[54] SAFETY HARNESS DEVICE

[76] Inventor: Margaret J. Freemon, 3118 Colyar Dr., Chattanooga, Tenn. 37404

[21] Appl. No.: 13,419

[22] Filed: Feb. 21, 1979

Related U.S. Application Data

[63] Continuation-in-part of Ser. No. 953,874, Oct. 23, 1978, abandoned.

[51] Int. Cl.³ ................................................ B63C 9/08
[52] U.S. Cl. ............................................ 9/336; 182/3; 119/96
[58] Field of Search .................... 9/310 J, 310 R, 312, 9/313, 329, 334, 336, 338, 337, 340, 14; 119/96; 182/3; 35/29 B; 272/71; 244/151R

[56] References Cited

U.S. PATENT DOCUMENTS

| 655,373 | 8/1900 | Roden | 9/337 |
| 661,457 | 11/1900 | Plummer | 9/336 |
| 2,368,558 | 1/1945 | Maloney | 9/14 |
| 2,699,284 | 1/1955 | Rose | 119/96 |
| 2,887,786 | 5/1959 | Moran | 244/151 R |
| 2,956,541 | 10/1960 | Rall | 119/96 |
| 3,077,292 | 2/1963 | Gehrke | 119/96 |
| 3,452,374 | 7/1969 | Turner | 244/151 R |

OTHER PUBLICATIONS

Atlas Safety Equipment Company, Inc., Catalogue #65, p. 8.

Primary Examiner—Trygve M. Blix
Assistant Examiner—Jesus D. Sotelo
Attorney, Agent, or Firm—Stevens, Davis, Miller & Mosher

[57] ABSTRACT

A harness device for supporting a person, such as a child or mentally or physically impaired person, in the water includes a wide chest band which is adjustable in length and lockable in any adjusted position. The device also includes a pair of shoulder straps secured to the upper end of the chest band on opposite sides thereof and which are adapted to extend over the person's shoulders. Each of the shoulder straps is adjustable in length and lockable in any adjusted position. The harness device also includes a pair of leg straps secured to the lower end of the chest band and adapted to extend around the person's legs at the crotch. Each of the leg straps is also adjustable in length and lockable in any adjusted position. The opposite ends of one of the leg straps is directly secured to one side of the chest band and the opposite ends of the other one of the leg straps is directly secured to the other side of the chest band. The device also includes a hand grip secured to the back of the chest band. The grip includes a strap directly secured at one end to a portion of the chest band adjacent the upper end thereof and secured at its other end to a portion of the chest band adjacent the lower end thereof. The device also includes a ring secured to the back of the chest band between it and the hand grip, a guide line secured at one end to the ring, and a handle secured to the other end of the guide line. The guide line is adjustable in length. With the hand grip and/or the guide line and handle, an adult, while remaining in a comfortable upright position, can easily support and be in control of the movements of the person, such as a child, in the water. A floatation device may be detachably secured to the chest band. In alternative embodiments, the lower edge of the chest band is secured to the upper edge of shorts, such as swimming shorts.

12 Claims, 9 Drawing Figures

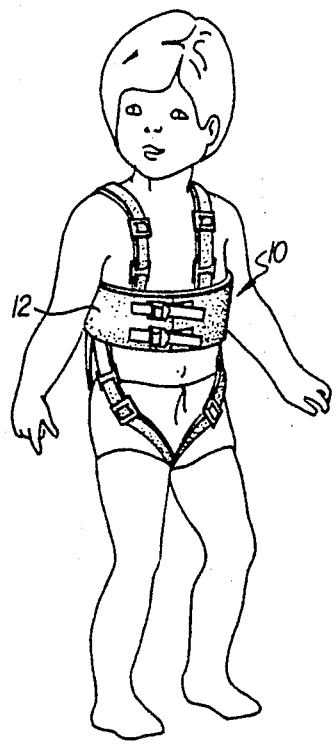
Fig. 1
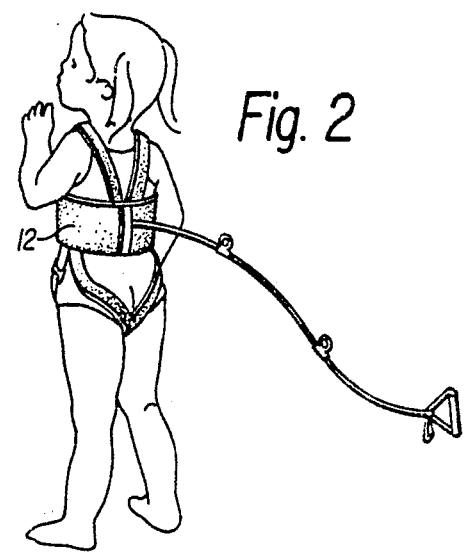
Fig. 2
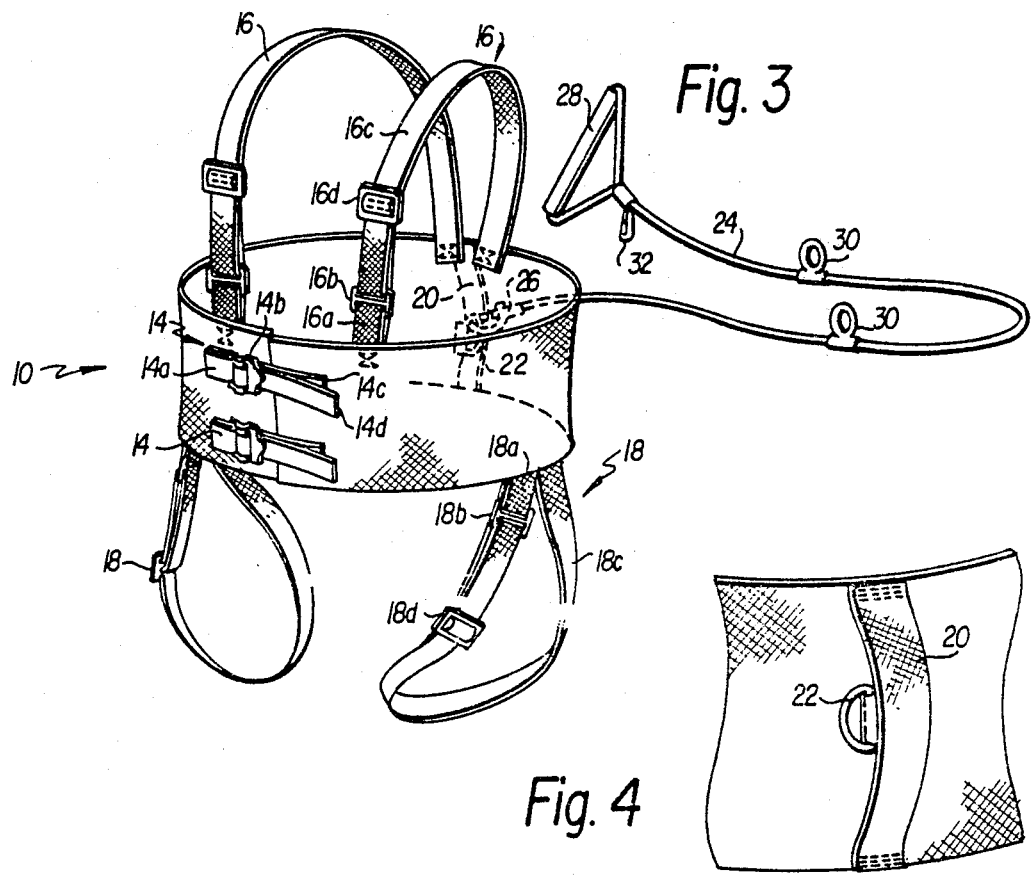
Fig. 3
Fig. 4

SAFETY HARNESS DEVICE

CROSS REFERENCE TO RELATED APPLICATION

This application is a continuation-in-part of Applicant's U.S. Pat. application Ser. No. 953,874, filed Oct. 23, 1978, now abandoned.

BACKGROUND OF THE INVENTION

This invention relates to a harness device and more particularly to a harness device for supporting a person, such as a child or mentally or physically impaired person, in the water so that the person can be supported or controlled by an adult. The invention is particularly suitable for use in teaching children to swim because the invention enables an adult to stand erect and not injure or strain the back while the adult easily controls the person's movement in the water.

It is an object of this invention to provide a safety harness device for a person which is safe and reliable.

It is a further object of this invention to provide a safety harness device which can be easily gripped and controlled by an adult, without back strain.

It is a further object of this invention to provide a safety harness device which is comfortable to the person wearing it and does not restrict his body movements in any way.

It is a further object of this invention to provide a safety harness device which can be easily manufactured.

It is a further object of this invention to provide a light-weight and inexpensive safety harness device.

It is a further object of this invention to provide a light-weight and inexpensive safety harness device with an attached floatation device which will support the user in the water.

It is a further object of this invention to provide a safety harness device which can be used safely and with confidence by adults to give children and mentally or physically impaired persons swimming instructions and water exercises without fear that the person's movements cannot be controlled in the water.

The above objects and others are obtained with the invention by providing a safety harness device which includes a wide chest band adjustable in length and lockable in any adjusted position; a pair of shoulder straps secured to the upper end of the chest band on opposite sides thereof and adapted to extend over the person's shoulders, which shoulder straps are adjustable in length and lockable in any adjusted position; a pair of leg straps secured to the lower end of the chest band and adapted to extend around the person's legs at the crotch, which leg straps are adjustable in length and lockable in any adjusted position with the opposite ends of one of the leg straps being directly secured to one side of the chest band and the opposite ends of the other of said leg straps being directly secured to the other side of the chest band; a hand grip secured to the back of the chest band and comprising a strap directly secured at one end to a portion of the chest band adjacent the upper end thereof and secured at its other end to a portion of the chest band adjacent the lower end thereof; a ring secured to the back of the chest band between it and the hand grip; a guide line adjustable in length secured at one end to the ring; and a handle secured to the other end of the guide line. The safety harness device may also include a flotation device which may be detachably secured for example to the chest band.

Also, the chest band may be secured at its lower edge to the upper edge of shorts, such as swimming shorts, which may be provided in place of the leg straps described above.

BRIEF DESCRIPTION OF THE DRAWINGS

FIG. 1 is a front view of a child wearing a safety harness device of the invention;

FIG. 2 is a rear view of a child wearing the safety harness device of the invention;

FIG. 3 is a perspective view, on an enlarged scale, of the safety harness device of the invention;

FIG. 4 is a perspective view, on an enlarged scale, of a detail of the invention shown in FIGS. 2 and 3;

DESCRIPTION OF THE PREFERRED EMBODIMENT

Figure 5:
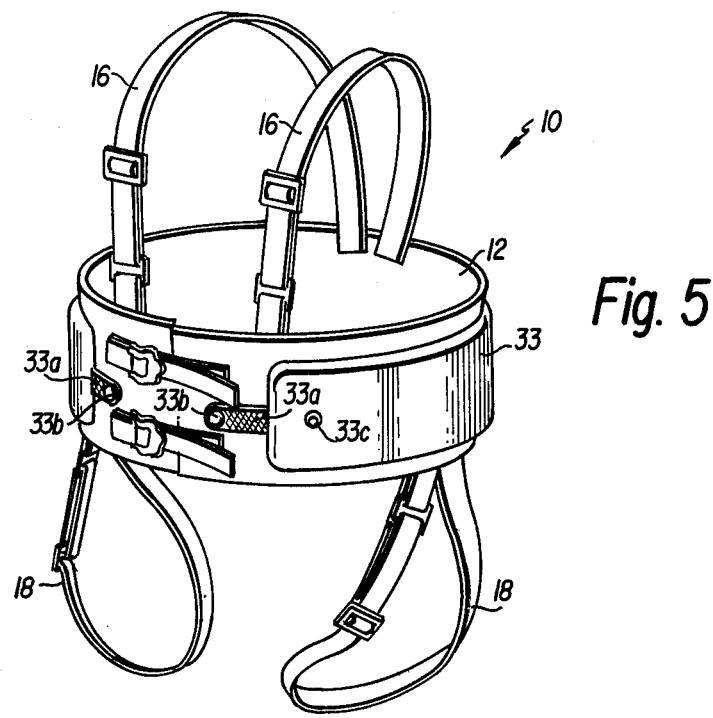
FIG. 5 is a view similar to FIG. 3, but additionally showing the floatation device on the chest band.

As shown in FIGS. 1 through 3, the safety harness device 10 includes a wide chest band 12. The chest band 12 is adjustable in length by a pair of adjustable straps 14. Each strap 14 includes a first portion 14a which is threaded through one section of a two piece rapid release buckle 14b and is secured, for example, by stitching both ends together to chest band 12. Each strap 14 also includes a second strap portion 14c. The portion 14c is secured, for example, by stitching at one end to the other end of the chest band 12 and is threaded through the locking mechanism in the other end of the two piece rapid release buckle 14b and terminates in a free end 14d. By threading the portion 14c through the buckle and pulling the end 14d away from the buckle 14b, the straps 14 can be used to adjust the length of the chest band 12 so as to be snugly disposed about the chest of the child or other person wearing the safety harness device. In any adjusted position of the chest band 12, the buckles 14b securely lock the chest band 12 in adjusted position.

The safety harness device 10 also includes a pair of shoulder straps 16 on opposite sides of the chest band 12. The straps 16 are adapted to extend over the child's or other person's shoulders. The straps 16 are adjustable in length so as to snugly be disposed over the person's shoulders. Each strap 16 includes a first strap portion 16a which is threaded through a ring ladder 16b and is secured, for example, by stitching both ends to the upper front edge of the chest band 12. Each strap 16 also includes a second strap portion 16c. Each portion 16c is secured at one end, for example, by stitching to the upper back edge of the chest band 12. The portion 16c extends from its connection to the chest band 12 up over the shoulders of the person and is threaded through a ladder clamp member 16d and through ring ladder 16b and back up to and fixedly secured to the central post of the ladder clamp 16d. By adjustably moving the clamp 16d along the strap portion 16c, the length of the straps 16 can be adjusted. By virtue of the ladder clamp 16d, the strap 16 is locked in any adjusted position.

The safety harness device also includes a pair of leg straps 18. Both ends of each of the leg straps are secured to opposite sides of the lower edge of the chest band 12, for example, by stitching. Each leg strap 18 includes a first strap portion 18a which is threaded through a ring ladder 18b and is secured, for example, by stitching both ends to the lower side edge of chest band 12. Each leg strap also includes a second strap member 18c which is secured, for example, by stitching to the lower edge of the chest band 12 adjacent to strap 18a, and is then adapted to be disposed around the person's leg at the crotch and up through a ladder clamp member 18d and continuing on and threaded through ring ladder 18b and back to and secured to the central post of ladder clamp 18d. By moving the clamp 18d along the strap portion 18c, the length of each of the leg straps 18 can be adjusted. The clamp 18d functions to securely lock each leg strap 18 in any adjusted position.

With particular reference to FIG. 4, the safety harness device also includes a hand grip 20 which is secured to the center back of the chest band. The hand grip 20 comprises a strap which is directly secured, for example, by stitching at one end to a portion of the chest band 12 adjacent the upper edge thereof and is secured at its other end for example by stitching to a portion of the chest band 12 adjacent the lower edge thereof. An adult can grip the hand grip 20 and thereby help control the movement of the child or other person in the water. Since the hand grip is directly secured to the chest band and because the chest band is quite wide, i.e., unlike a conventional strap or belt, the adult can adequately control the child's movement by simply gripping the hand grip.

The safety harness device also includes a D-ring 22 which is secured, for example, by stitching a short piece of material wound through the ring to the back of the chest band 12. Advantageously, for better balance, the ring is positioned in the center back of the chest band.

The safety harness device also includes a guide line 24 which can be secured by means of a conventional spring clip type fastener 26 to the D-ring 22. A swivel type handle 28 is secured to the other end of the guide line 24. A plurality of rings 30 are fixedly secured along the guide line 24. A conventional spring clip 32 can be disposed adjacent the handle 28. By selectively hooking the clip 32 over the rings 30, the length of the guide line 24 can be adjusted to thereby obtain different degrees of control of the person in the water by the person holding the handle 28. When an adult grips the handle 28 instead of the hand grip 20, the person wearing the safety harness device is of course given more freedom of movement in the water. At the same time, the adult or other person is able to maintain complete control of the child or other person in the safety harness device. Should the child or other person wearing the device lose control of their body movements in the water, the adult gripping the handle can pull the child or other person toward them and otherwise control the movements of the child very quickly. If it is desired to use only the hand grip 20 to control the child or other person, the guide line 24 can be easily detached from the ring 22 by means of the clip 26.

It should be apparent from the above description of the invention that the safety harness device can be easily and snugly disposed about a person's body without in any way restricting the movement of the arms, legs and head of that person. Also, with the invention, the hand grip 20 as well as the handle 28 provide a simple and yet effective means of controlling the person wearing the safety harness device in the water.

Figure 6:
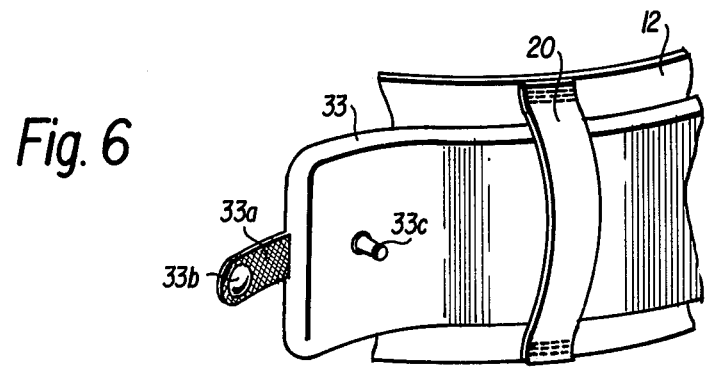
FIG. 6 is a view similar to FIG. 4, but additionally showing the floatation device.

As shown in FIGS. 5 and 6, an easily detachable floatation device 33, in the form of a blow-up tube, may be readily attachable to and detachable from the chest band 12. A short strap 33a on each end of the tube 33 is provided with a gripper type fastener 33b which can be readily snapped onto the chest band 12. As shown in FIG. 6, the tube 33 can be passed through the hand grip 20 when mounting it onto the chest band 12. The tube 33 has a valve 33c through which the tube can be inflated by either an air pump or can be blown up by a person.

With the readily detachable floatation device, the versatility of the safety harness device is increased in that it may be used with or without the floatation device, depending on the use and/or the desire of the user. For instance, for only playing in the water or for beginning swimming instruction, the floatation device may be attached to the safety harness device; whereas, for advanced swimming instruction, it might be desirable to detach the floatation device from the chest band.

Figure 7:
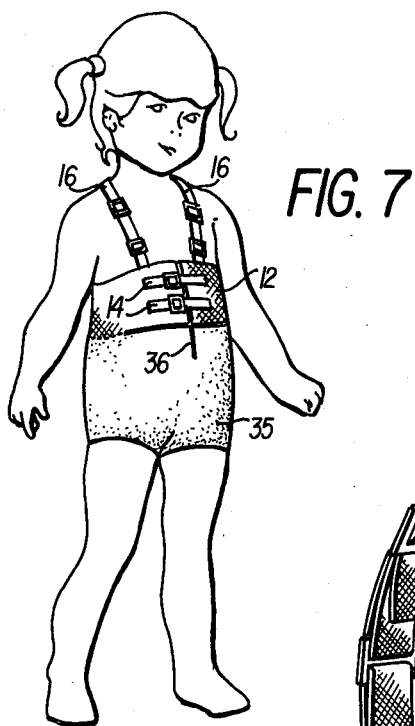
FIG. 7 is a perspective of another embodiment of the invention.
Figure 8:
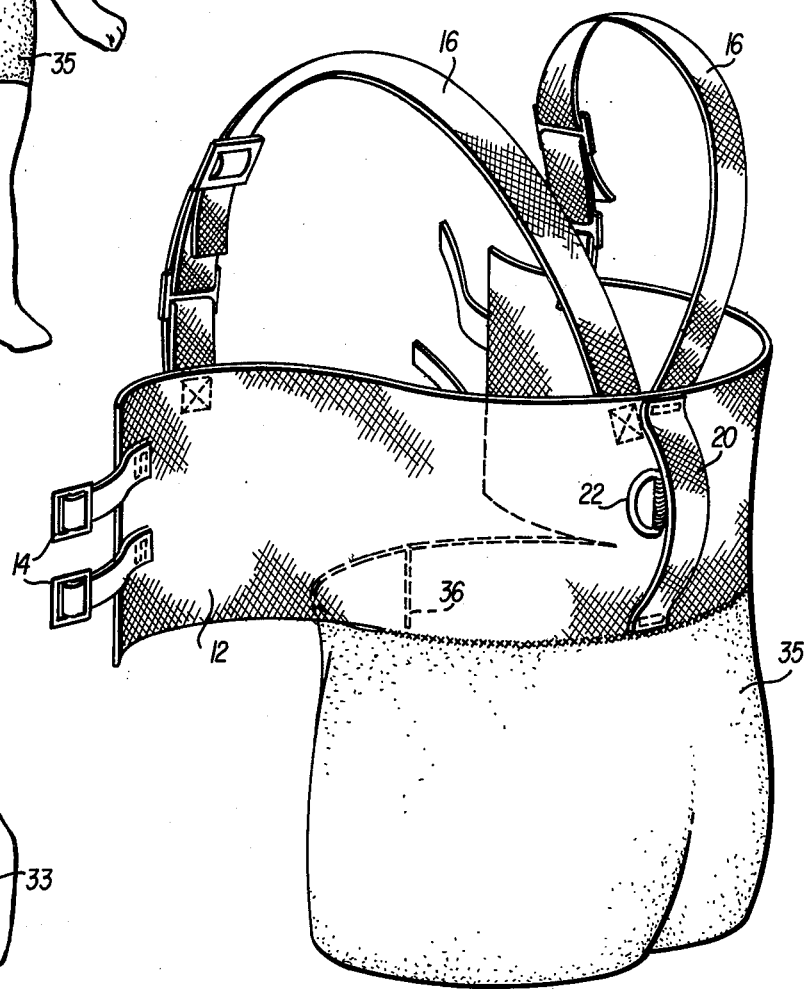
FIG. 8 is a perspective view, on an enlarged scale, of the invention shown in FIG. 7.

Another embodiment of the invention is shown in FIGS. 7 through 8. The same reference numerals are used in those FIGS. to designate identical parts described above. In view of that description, the following description is generally limited to the features of the invention in this embodiment which differ from those described above.

In the embodiment of FIGS. 7 and 8, the lower edge of the chest band 12 is fixedly secured, for example, by stitching (FIG. 8), to the upper edge of a pair of shorts 35 having a small slit 36 at the front. The stitching, as shown in FIG. 8, is made to extend from one side of the shorts around the back past the handle 20 and terminate at the other side.

Figure 9:
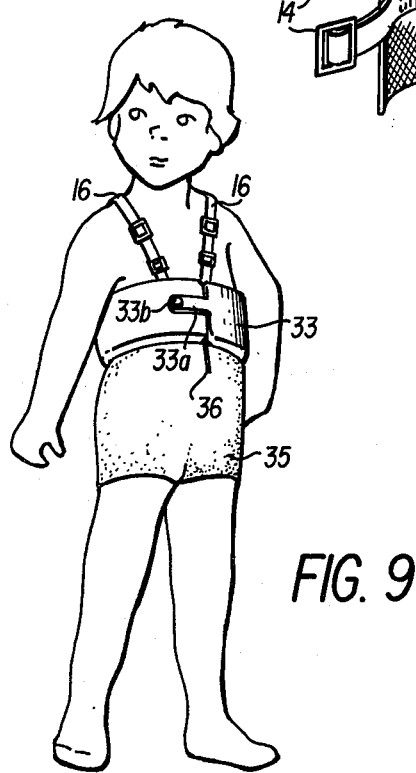
FIG. 9 is a view similar to FIG. 7, but additionally showing a floatation device on the chest band.

As shown in FIG. 9, a floatation device 33 may be readily attachable to and detachable from the chest band 12 in the manner shown and described above with respect to the embodiments of FIGS. 5 and 6. As in the embodiment of FIG. 6, in the embodiment of FIG. 9, the floatation device 33 can be passed through the hand grip 20 when mounting it on the chest band 12.

Advantageously, the chest band 12, and straps 14, 16 and 18 can be made of nylon webbing which is substantially non-stretchable, will not corrode and is comfortable to the wearer. It is particularly important that the chest band 12 be made of a substantially non-stretchable material since otherwise control of the child or other person could be lost if the chest band were stretched to any substantial extent. Similarly, the guide line 24 can be made of nylon rope. The various fasteners such as the clamps 14b, 16b, 18b and 18d, and the clips 26 and 32 as well as the handle 28 and the ring 22 can be made of a strong plastic or metal material which will not corrode. It will, of course, occur to persons ordinarily skilled in the art that the various parts of the invention could be made of other materials which will not corrode in water and yet will be of sufficient strength to achieve the objects of applicant's invention.

The length adjustability of the guide line 24 permits an adult handling a child or other person wearing the safety harness device to stand erect in any comfortable depth of water while maintaining proper tension on the line to control the child or other person. The handle can be held by someone standing for example at the edge of a pool while the child or other person wearing the safety harness device is in the water.

Although the floatation device 33 is described above as being of the blow-up type, it is contemplated that other types of floatation devices, such as the solid foam or plastic type, could be used in the invention.

Although the invention has been described above with reference to particular preferred embodiments thereof, it should be apparent to persons skilled in the art that various modifications can be made to the invention without departing from the scope of the invention as defined in the claims.

What is claimed and intended to be secured by Letters Patent is:

1. A safety harness device for supporting a person in the water for swimming instruction, said device comprising:
   a one-piece wide chest band adjustable in length, adapted to snugly surround the person's chest with its upper edge adjacent the arm pits of the person and its lower edge adjacent the waist of the person, and made of substantially non-stretchable material;
   a pair of shoulder straps secured to the upper edge of the chest band and adapted to extend over the person's shoulders, each of said shoulder straps being adjustable in length;
   a pair of leg straps secured to the lower edge of the chest band and adapted to extend around the person's legs at the crotch, each of said leg straps being adjustable in length; and
   a vertically extending hand grip secured to the exterior of the back of said chest band at the center thereof which can be gripped by an adult to help control the person's movement in the water, the upper end of the hand grip being secured adjacent the upper edge of the chest band and the lower end of the hand grip being secured adjacent the lower edge of the chest band.

2. A safety harness device for supporting a person in the water for swimming instruction, said device comprising:
   a one-piece wide chest band adjustable in length, lockable in any adjusted position, and made of substantially non-stretchable material, said chest band being adapted to snugly surround the person's chest with its upper edge adjacent the arm pits of the person and its lower edge adjacent the waist of the person;
   a pair of shoulder straps secured to the upper edge of the chest band on opposite sides thereof and adapted to extend over the person's shoulders, each of said shoulder straps being adjustable in length and lockable in any adjusted position;
   a pair of leg straps secured to the lower edge of the chest band on opposite sides thereof and adapted to extend around the person's legs at the crotch, each of said leg straps being adjustable in length and lockable in any adjusted position; and
   a vertically extending hand grip secured to the exterior of the back of the chest band at the center thereof, said grip comprising a vertically extending strap secured at one end to a portion of the chest band adjacent the upper edge thereof and secured at its other end to a portion of the chest band adjacent the lower edge thereof.

3. A safety harness device for supporting a person in the water for swimming instruction, said device comprising:
   a one-piece wide chest band adjustable in length, lockable in any adjusted position, and made of substantially non-stretchable material, said chest band being adapted to snugly surround the person's chest with its upper edge adjacent the arm pits of the person and its lower edge adjacent the waist of the person;
   a pair of shoulder straps secured to the upper edge of the chest band on the opposite sides thereof and adapted to extend over the person's shoulders, each of said straps being adjustable in length and lockable in any adjusted position;
   a pair of leg straps secured to the lower edge of the chest band and adapted to extend around the person's legs at the crotch, each of said leg straps being adjustable in length and lockable in any adjusted position, the opposite ends of one of said legs straps being directly secured to one side of the chest band and the opposite ends of the other of said legs straps being directly secured to the other side of the chest band;
   a vertically extending hand grip secured to the exterior of the back of the chest band at the center thereof, said grip comprising a vertically extending strap directly secured at one end to a portion of the chest band adjacent the upper edge thereof and secured at its other end to a portion of the chest band adjacent the lower edge thereof;
   a ring secured to the back of the chest band;
   a guide line secured at one end to said ring, said line being adjustable in length; and
   a handle secured to the other end of the guide line.

4. A safety harness device for supporting a person in the water for swimming instruction, said device comprising:
   a one-piece wide chest band adjustable in length, adapted to snugly surround the person's chest with its upper edge adjacent the arm pits of the person and its lower edge adjacent the waist of the person, and made of substantially non-stretchable material;
   a floatation device detachably secured to said chest band;
   a pair of shoulder straps secured to the upper edge of the chest band and adapted to extend over the person's shoulders, each of said shoulder straps being adjustable in length;
   a pair of leg straps secured to the lower edge of the chest band and adapted to extend around the person's legs at the crotch, each of said leg straps being adjustable in length; and
   a vertically extending hand grip secured to the exterior of the back of said chest band at the center thereof which can be gripped by an adult to help control the person's movement in the water, the upper end of said hand grip being secured adjacent the upper edge of the chest band and the lower end of said hand grip being secured adjacent the lower edge of said chest band.

5. A safety harness device for supporting a person in the water for swimming instruction, said device comprising:
   a one-piece wide chest band adjustable in length, lockable in any adjusted position, and made of substantially non-stretchable material, said chest band being adapted to snugly surround the person's chest with its upper edge adjacent the arm pits of the person and its lower edge adjacent the waist of the person;

a floatation device detachably secured to said chest band;

a pair of shoulder straps secured to the upper edge of the chest band on opposite sides thereof and adapted to extend over the person's shoulders, each of said shoulder straps being adjustable in length and lockable in any adjusted position;

a pair of leg straps secured to the lower edge of the chest band on opposite sides thereof and adapted to extend around the person's legs at the crotch, each of said leg straps being adjustable in length and lockable in any adjusted position; and a vertically extending hand grip secured to the exterior of the back of the chest band at the center thereof, said grip comprising a vertically extending strap secured at one end to a portion of the chest band adjacent the upper edge thereof and secured at its other end to a portion of the chest band adjacent the lower edge thereof.

6. A safety harness device for supporting a person in the water for swimming instruction, said device comprising:

a one-piece wide chest band adjustable in length, lockable in any adjusted position, and made of substantially non-stretchable material, said chest band being adapted to snugly surround the person's chest with its upper edge adjacent the arm pits of the person and its lower edge adjacent the waist of the person;

a pair of shoulder straps secured to the upper edge of the chest band on opposite sides thereof and adapted to extend over the person's shoulders, each of said straps being adjustable in length and lockable in any adjusted position;

a pair of leg straps secured to the lower edge of the chest band and adapted to extend around the person's legs at the crotch, each of said leg straps being adjustable in length and lockable in any adjusted position, the opposite ends of one of said leg straps directly secured to one side of the chest band and the opposite ends of the other of said leg straps being directly secured to the other side of the chest band;

a vertically extending hand grip secured to the exterior of the back of the chest band at the center thereof, said grip comprising a vertically extending strap directly secured to one end to a portion of the chest band adjacent the upper edge thereof and secured at its other end to a portion of the chest band adjacent the lower edge thereof;

an elongated floatation device detachably secured to and extending around the exterior of said chest band from substantially one end thereof to the other; said hand grip extending over said floatation device;

a ring secured to the back of the chest band;

a guide line secured at one end to said ring, said line being adjustable in length; and a handle secured to the other end of the guide line.

7. A safety harness device for supporting a person in the water for swimming instruction, said device comprising:

a one-piece wide chest band adjustable in length, adapted to snugly surround the person's chest with its upper edge adjacent the arm pits of the person and its lower edge adjacent the waist of the person, and made of substantially non-stretchable material;

a pair of shoulder straps secured to the upper edge of the chest band and adapted to extend over the person's shoulders, each of said shoulder straps being adjustable in length;

shorts, the upper edge of which is secured to the lower edge of the chest band; and a vertically extending hand grip secured to the exterior of the back of the said chest band at the center thereof which can be gripped by an adult to help control the person's movements in the water, the upper end of the hand grip being secured adjacent the upper edge of the chest band and the lower end of the hand grip being secured adjacent the lower edge of the chest band.

8. A safety harness device for supporting a person in the water for swimming instruction, said device comprising:

a one-piece wide chest band adjustable in length, lockable in any adjusted position, and made of substantially non-stretchable material, said chest band being adapted to snugly surround the person's chest with its upper edge adjacent the arm pits of the person and its lower edge adjacent the waist of the person;

a pair of shoulder straps secured to the upper edge of the chest band on opposite sides thereof and adapted to extend over the person's shoulders, each of said straps being adjustable in length and lockable in any adjusted position;

shorts, the upper edge of which is fixedly secured to the lower edge of the chest band at the back and on the opposite sides thereof; and a vertically extending hand grip secured to the exterior of the back of the chest band at the center thereof, said grip comprising a vertically extending strap secured at one end to a portion of the chest band adjacent the upper edge thereof and secured at its other end to a portion of the chest band adjacent the lower edge thereof.

9. A safety device for supporting a person in the water for swimming instruction, said device comprising:

a one-piece wide chest band adjustable in length, lockable in any adjusted position, and made of substantially non-stretchable material, said chest band being adapted to snugly surround the person's chest with its upper edge adjacent the arm pits of the person and its lower edge adjacent the waist of the person;

a pair of shoulder straps secured to the upper edge of the chest band on opposite sides thereof and adapted to extend over the person's shoulders, each of said straps being adjustable in length and lockable in any adjusted position;

shorts, the upper edge of which is fixedly secured to the lower edge of the chest band at the back and on the opposite sides thereof;

a vertically extending hand grip secured to the exterior of the back of the chest band at the center thereof, said grip comprising a vertically extending strap directly secured at one end to a portion of the chest band adjacent the upper edge thereof and secured at its other end to a portion of the chest band adjacent the lower edge thereof;

a ring secured to the back of the chest band;

a guide line secured at one end to said ring, said line being adjustable in length; and a handle secured to the other end of the guide line.

10. A safety harness device for supporting a person in the water for swimming instruction, said device comprising:
- a one-piece wide chest band adjustable in length, adapted to snugly surround the person's chest, and made of substantially non-stretchable material, said chest band being adapted to snugly surround the person's chest with its upper edge adjacent the arm pits of the person and its lower edge adjacent the waist of the person;
- a floatation device detachably secured to said chest band;
- a pair of shoulder straps secured to the upper edge of the chest band and adapted to extend over the person's shoulders, each of said shoulder straps being adjustable in length;
- shorts, the upper edge of which is secured to the lower edge of the chest band; and
- a vertically extending hand grip secured to the exterior of the back of said chest band at the center thereof which can be gripped by an adult to help control the person's movements in the water, the upper end of said hand grip being secured adjacent the upper edge of the chest band and the lower end of said hand grip being secured adjacent the lower edge of the chest band.

11. A safety harness device for supporting a person in the water for swimming instruction, said device comprising:
- a one-piece wide chest band adjustable in length, lockable in any adjusted position, and made of substantially non-stretchable material, said chest band being adapted to snugly surround the person's chest with its upper edge adjacent the arm pits of the person and its lower edge adjacent the waist of the person;
- a floatation device detachably secured to said chest band;
- a pair of shoulder straps secured to the upper edge of the chest band on opposite sides thereof and adapted to extend over the person's shoulders, each of said shoulder straps being adjustable in length and lockable in any adjusted position;
- shorts, the upper edge of which is fixedly secured to the lower edge of the chest band at the back on the opposite sides thereof; and
- a vertically extending hand grip secured to the exterior of the back of the chest band at the center thereof, said grip comprising a vertically extending strap secured at one end to a portion of the chest band adjacent the upper edge thereof and secured at its other end to a portion of the chest band adjacent the lower edge thereof.

12. A safety harness device for supporting a person in the water for swimming instruction, said device comprising:
- a one-piece wide chest band adjustable in length, lockable in any adjusted position, and made of substantially non-stretchable material, said chest band being adapted to snugly surround the person's chest with its upper edge adjacent the arm pits of the person and its lower edge adjacent the waist of the person;
- a pair of shoulder straps secured to the upper edge of the chest band on opposite sides thereof and adapted to extend over the person's shoulders, each of said straps being adjustable in length and lockable in any adjusted position;
- shorts, the upper edge of which is fixedly secured to the lower edge of the chest band at the back and on the opposite sides thereof;
- a vertically extending hand grip secured to the exterior of the back of the chest band at the center thereof, said grip comprising a vertically extending strap directly secured at one end to a portion of the chest band adjacent the upper edge thereof and secured at its other end to a portion of the chest band adjacent the lower edge thereof;
- an elongated floatation device detachably secured to and extending around the exterior of said chest band from substantially one end thereof to the other, said hand grip extending over said floatation device;
- a ring secured to the back of the chest band;
- a guide line secured at one end to said ring, said line being adjustable in length; and
- a handle secured to the other end of the guide line.

* * * * *